(12) United States Patent
Shroff et al.

(10) Patent No.: US 10,401,604 B2
(45) Date of Patent: Sep. 3, 2019

(54) RESOLUTION ENHANCEMENT FOR LIGHT SHEET MICROSCOPY SYSTEMS AND METHODS

(71) Applicants: The United States of America, as Represented by the Secretary, Dept. of Health and Human Services, Rockville, MD (US); Hari Shroff, Rockville, MD (US); Yicong Wu, Rockville, MD (US); Sara Abrahamsson, Rockville, MD (US)

(72) Inventors: Hari Shroff, Rockville, MD (US); Yicong Wu, Rockville, MD (US); Sara Abrahamsson, Rockville, MD (US)

(73) Assignee: The United States of America, as Represented by the Secretary, Department of Health and Human Services, Bethesda, MD (US)

( * ) Notice: Subject to any disclaimer, the term of this patent is extended or adjusted under 35 U.S.C. 154(b) by 91 days.

(21) Appl. No.: 15/511,580

(22) PCT Filed: Sep. 24, 2015

(86) PCT No.: PCT/US2015/052047
§ 371 (c)(1),
(2) Date: Jul. 25, 2017

(87) PCT Pub. No.: WO2016/049368
PCT Pub. Date: Mar. 31, 2016

(65) Prior Publication Data
US 2017/0336610 A1 Nov. 23, 2017

Related U.S. Application Data

(60) Provisional application No. 62/054,484, filed on Sep. 24, 2014.

(51) Int. Cl.
*G01N 1/00* (2006.01)
*G02B 21/00* (2006.01)
(Continued)

(52) U.S. Cl.
CPC ..... *G02B 21/0072* (2013.01); *G01N 21/6458* (2013.01); *G02B 21/0044* (2013.01);
(Continued)

(58) Field of Classification Search
CPC .......... G01N 21/64; G01N 21/6402; G01N 21/6404; G01N 21/6408; G01N 21/6428; G01N 21/6458
See application file for complete search history.

(56) References Cited

U.S. PATENT DOCUMENTS 9,477,091 B2    10/2016    Abrahamsson
2009/0231689 A1    9/2009    Pittsyn
(Continued)

OTHER PUBLICATIONS

Supplementary European Search Report issued in corresponding European Patent Application No. 15843742.6, dated Apr. 24, 2018, 12 pages.
(Continued)

*Primary Examiner* — David P Porta
*Assistant Examiner* — Mamadou Faye
(74) *Attorney, Agent, or Firm* — Polsinelli PC

(57) ABSTRACT

Embodiments of a resolution enhancement technique for a light sheet microscopy system having a three objective lens arrangement in which one objective lens illuminates a sample and the second and third objective lenses collect the fluorescence emissions emitted by the sample are disclosed. The second objective lens focuses a first portion of the fluorescence emissions for detection by a second detection component, while the third objective lens focuses a second portion of the fluorescence emissions through a diffractive or
(Continued)

refractive optic component for detection by a first detector component. A processor combines the images resulting from the first and second portions of the fluorescence emissions for generating composite images with increased axial and lateral resolution.

20 Claims, 7 Drawing Sheets

(51) Int. Cl.
G02B 21/16 (2006.01)
G01N 21/64 (2006.01)
G02B 21/18 (2006.01)
G02B 27/00 (2006.01)
G02B 21/10 (2006.01)
G02B 27/42 (2006.01)

(52) U.S. Cl.
CPC ......... *G02B 21/0076* (2013.01); *G02B 21/10* (2013.01); *G02B 21/16* (2013.01); *G02B 21/18* (2013.01); *G02B 27/0075* (2013.01); *G02B 27/42* (2013.01); *G01N 2021/6463* (2013.01); *G01N 2201/06113* (2013.01)

(56) References Cited

U.S. PATENT DOCUMENTS

| 2011/0115895 | A1 | 5/2011 | Huisken | |
|---|---|---|---|---|
| 2012/0206798 | A1* | 8/2012 | Knop | G02B 21/002 359/385 |
| 2012/0307326 | A1 | 12/2012 | Barbastathis | |
| 2013/0176622 | A1* | 7/2013 | Abrahamsson | G02B 21/367 359/571 |
| 2014/0099659 | A1* | 4/2014 | Keller | G01N 21/6486 435/29 |
| 2014/0126046 | A1* | 5/2014 | Shroff | G02B 21/0004 359/385 |
| 2014/0139840 | A1* | 5/2014 | Judkewitz | G02B 21/0056 356/456 |
| 2015/0022881 | A1* | 1/2015 | Loza Alvarez | G02B 21/06 359/385 |

OTHER PUBLICATIONS

International Search Report and Written Opinion issued in corresponding PCT Application No. PCT/US2015/052047, dated Jan. 6, 2016, 10 pages.
Abrahamsson, et al., Fast Multicolor 3D Imaging Using Aberration-Corrected Multifocus Microscopy, Nature Methods, vol. 10, No. 1, Jan. 2013, 6 pages.
Abrahamsson, et al., A New Approach to Extended Focus for High-Speed High-Resolution Biological Microscopy, SPIE BiOS, 2006, 9 pages.
Dufour, et al., Two-Photon Excitation Fluorescence Microscopy With a High Depth of Field Using an Axicon, Applied Optics, vol. 45, No. 36, Dec. 20, 2006, 7 pages.
Schmid, et al., High-Speed Panoramic Light-Sheet Microscopy Reveals Global Endodermal Cell Dynamics, Nature Communications 4, Jul. 25, 2013, 10 pages.

* cited by examiner

RESOLUTION ENHANCEMENT FOR LIGHT SHEET MICROSCOPY SYSTEMS AND METHODS

GOVERNMENT INTEREST STATEMENT

The present subject matter was made with U.S. government support. The U.S. government has certain rights in this subject matter.

FIELD

This document relates to methods and systems related to light sheet microscopy, and in particular, to resolution enhancement techniques for light sheet microscopy systems and methods.

BACKGROUND

Light sheet fluorescence microscopy uses parallelized excitation and a perpendicular geometry between excitation and detection to enable optically sectioned, high speed, volumetric imaging with massively reduced photo-damage and photo-bleaching compared to conventional imaging methods. Although this combination of benefits is enabling for biology, the spatial resolution of the light sheet microscopy has lagged behind other convention microscopy systems.

The main reason for the relatively poor resolution of light sheet microscopy is that the perpendicular geometry required necessitates the use of relatively low numerical aperture objectives. Acquiring images from multiple directions/views or using structured illumination to illuminate the sample in combination with image processing software does improve resolution, but these approaches fail to improve spatial resolution in light sheet microscopy applications to the extent possible in conventional microscopy, such as confocal microscopy. Furthermore, multi-view acquisition or structured illumination approaches have thus far required the sample to be exposed to more illumination than conventional, single-view light sheet fluorescence microscopy, thereby sacrificing some of the available signal/photon budget and mitigating the original advantages of light sheet fluorescence microscopy. In addition, such approaches require more images to be captured than a single-view light sheet fluorescence microscopy, thereby sacrificing the inherent speed.

As shown in FIG. 1, a conventional light sheet microscopy system, designated 10, is illustrated, in which a light sheet 18 generated from an illumination source (not shown), such as a laser source, is introduced into the sample (not shown) through a first objective lens 12. The illuminated sample emits fluorescence emissions 20 scattered at substantially a ninety degree angle relative to the light sheet 18 illuminating the sample and detected by a second objective lens 14. In particular, scanning the light sheet 18 through the first objective 12 while maintaining the focus in the second objective lens 14 generates an imaging volume of the sample. Although ninety degree detection ensures that the illumination plane defined through the sample is in focus, and that minimal out-of-focus light corrupts detection of the fluorescence emissions 20, it requires the use of relatively low NA optics. In addition, the majority of the fluorescence emissions excited by the light sheet 18 is scattered outside the aperture of the second objective 14 and wasted.

To collect a portion of the wasted fluorescence emissions 22, a third objective lens 16 may be positioned to capture some of the wasted fluorescence emissions 22 emitted by the sample. If the fluorescence emissions are imaged conventionally using only a tube lens and camera arrangement (e.g., conventional epifluorescence microscopy), relatively little of the fluorescence emissions 22 are used efficiently (i.e., "in focus"). This is because the depth of field of a high numerical objective is inversely proportional to the square of the numerical aperture.

Other techniques seek to capture more imaging planes at once and fusing them together to improve resolution relative to conventional light sheet fluorescence microscopy; however, such techniques suffer from out-of-focus light. As such, further improvements in the collection of fluorescence emissions in a light sheet microscopy system are desired.

BRIEF DESCRIPTION OF THE DRAWINGS

FIG. 6A is an image taken with the light sheet microscopy system of FIG. 5, while

Corresponding reference characters indicate corresponding elements among the view of the drawings. The headings used in the figures should not be interpreted to limit the scope of the claims.

DETAILED DESCRIPTION

Figure 1:
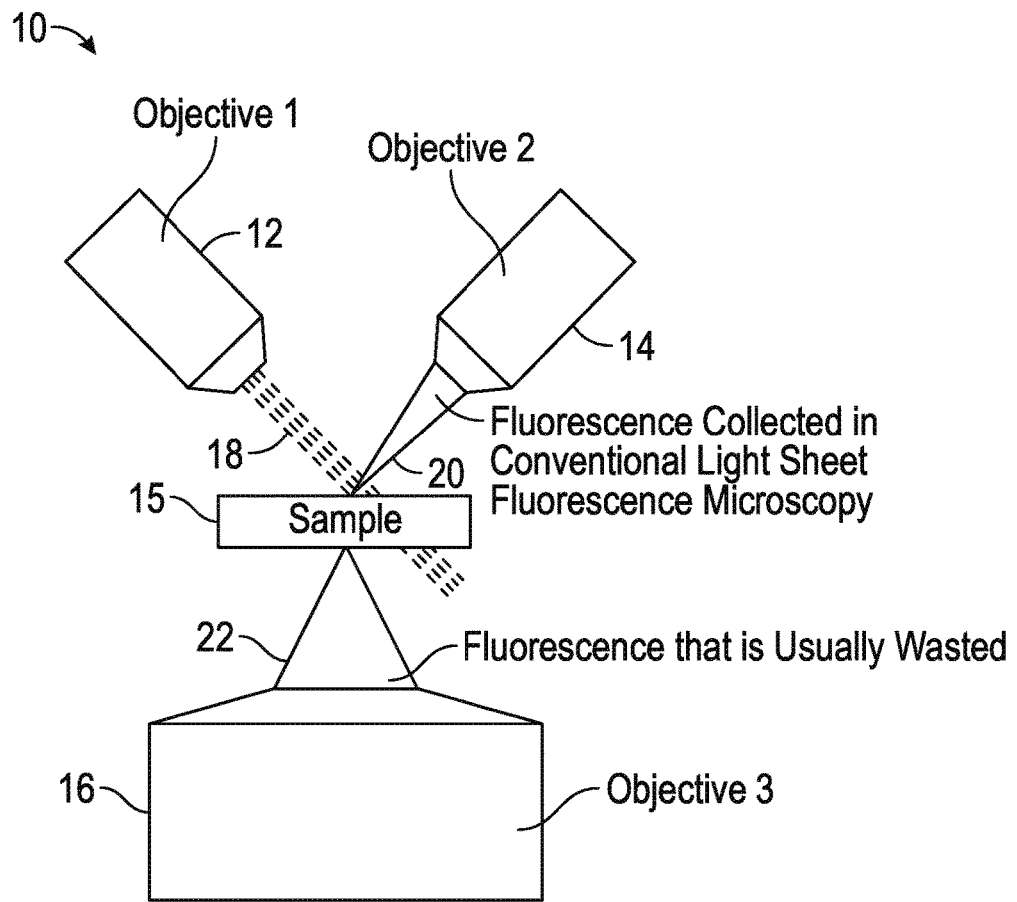
FIG. 1 is a simplified illustration showing a conventional light sheet microscopy system that uses a dual objective lens arrangement.

Various embodiments for applying a resolution enhancement technique for light sheet microscopy systems using a depth-of-focus optical arrangement to improve lateral resolution are disclosed. The resolution enhancement technique utilizes an arrangement of three objective lenses and a processor to combine images captured from one objective lens with images captured from another objective lens to enhance lateral resolution. Referring to the drawings, various embodiments of a light sheet microscopy system utilizing a resolution enhancement technique are illustrated and generally indicated as 100, 300 and 500 in FIGS. 2-8.

Figure 2:
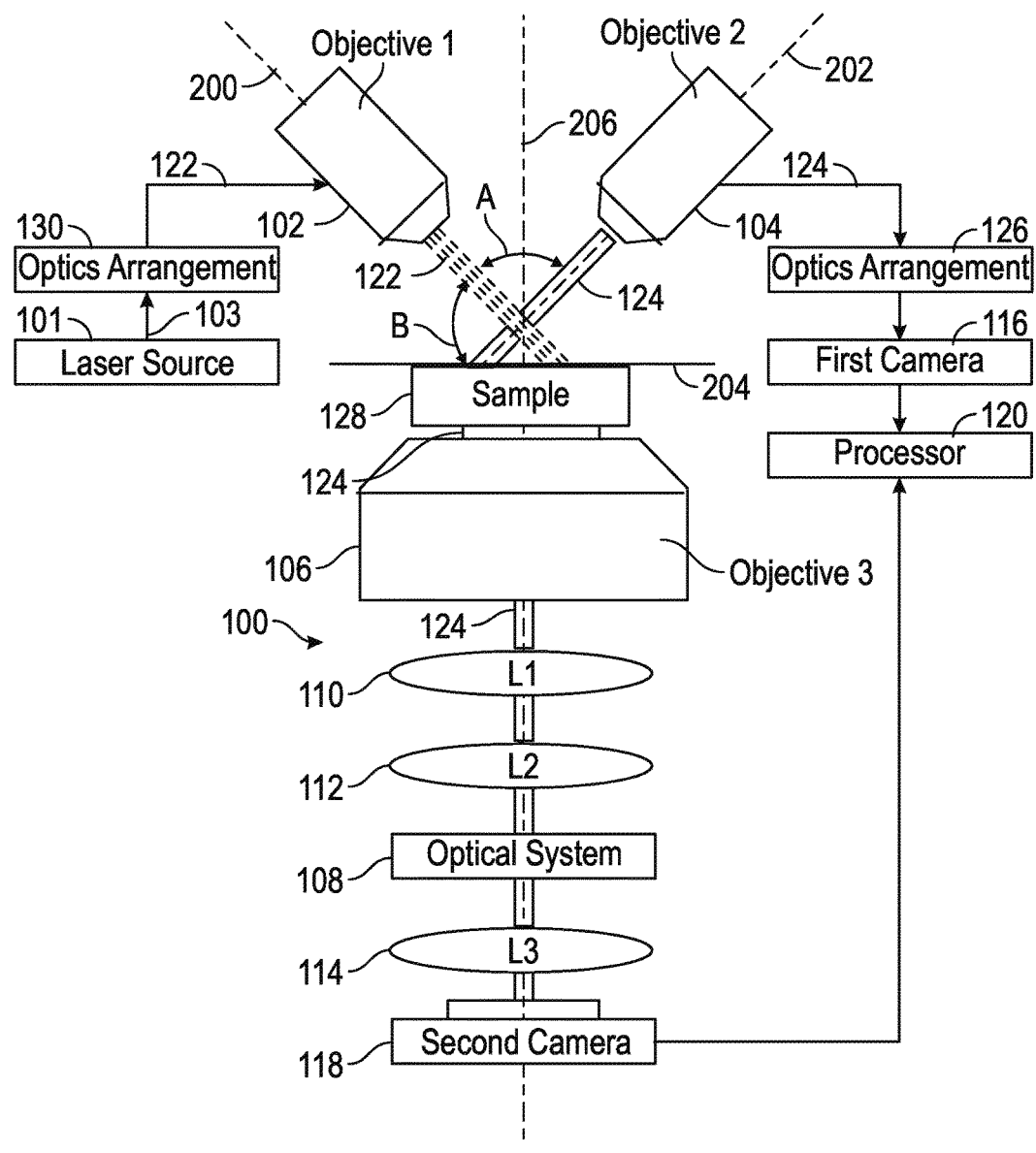
FIG. 2 is a simplified illustration showing one embodiment of a light sheet microscopy system that uses a dual objective lens arrangement having an extended depth-of-focus optical system.

As shown in FIG. 2, a simplified block diagram illustrates one embodiment of a light sheet microscopy system 100 that utilizes the resolution enhancement technique. In one embodiment, the light sheet microscopy system 100 may include an illumination source 101, for example a laser, that generates a single light beam 103 transmitted through an optics arrangement 130 for producing an excitation light sheet 122 that is focused through a first objective lens 102 for illuminating a sample 128. The first objective lens 102 defines a longitudinal axis 200 that forms at an angle B relative to the plane 204 of the sample 128. When the sample 128 is illuminated by the excitation light sheet 122 focused on the sample 128 through the first objective lens 102, fluorescence emissions 124 are generated by the sample 128 which are detected by a second objective lens 124 defining a longitudinal axis 202 that forms a perpendicular angle A relative to longitudinal axis 200 defined by the first objective lens 102. The second objective lens 104 focuses the fluorescence emissions 124 through an optics arrangement 126 for detection through a first camera 116. The detected images of the fluorescence emissions 124 are then sent to a processor 120 having one or more applications for processing the detected images of the fluorescence emissions 124.

As further shown in FIG. 2, fluorescence emissions 124 are also detected by a third objective lens 106 aligned along a longitudinal axis 206 that is in perpendicular relation to plane 204 of the sample 128. In one embodiment, the third objective lens 106 is a high numerical aperture objective lens. A first lens 110 and a second lens 112 may be arranged in 4f configuration so as to image the back focal plane of the third objective lens 106 at the back focal plane of the second lens 112.

In addition, an extended depth-of-focus optical system 108 for converting the fluorescence emissions 124 may be positioned between the second lens 112 and a third lens 114 to collapse the fluorescence emissions 124 focused by the third objective 106 to a single plane. This single plane formed by the fluorescence emissions 124 by the extended depth-of-focus optical system 108 may be imaged onto a second camera 118, for example a widefield detector, by the third lens 114, which is positioned one focal length away from the extended depth-of-focus optical system 108. In one embodiment, the second lens 112 and the third lens 114 are arranged in a 4f telescopic configuration.

In some embodiments, the extended depth-of-focus optical system 108 may be an incoherent "layer cake" optical arrangement or a cubic phase mask component. In some embodiments, the cubic phase mask component is a conventional diffractive optic that introduces strong aberration that dominates other aberrations, such as defocus, provides a much extended depth of field. Importantly, the cubic phase mask component preserves lateral resolution while degrading axial resolution, i.e. extending the depth of field, and therefore the cubic phase mask component has application in collecting fluorescence emissions 124 along a tilted imaging plane generated in the light sheet microscopy system 100.

In some embodiments, the incoherent "layer cake" optical arrangement may be a 'phase mask with circularly symmetric stair steps', such as a conventional refractive optic that enables incoherent addition of a series of annular sub-apertures which collectively fill the pupil of a high aperture third objective lens 106. The refractive optic produces an effect that creates a rotationally symmetric point-spread function with dramatically extended axial extent. When the incoherent "layer cake" optical arrangement is positioned in the (primary or secondary) back focal plane (e.g., Fourier plane) of the light sheet microscopy system 100, the incoherent "layer cake" optical arrangement can extend the axial depth of the field of the third objective lens 106.

In either embodiment of the extended depth-of-focus optical system 108 the depth of field is increased while largely preserving the lateral resolving power of the third objective lens 106. Any loss in lateral resolution may be compensated for by deconvolution. In some embodiments, other optics can provide extended depth of field could be used, such as an axicon or annular aperture.

In some embodiments, the third objective lens 106 may be arranged to both introduce the light sheet 122 into the sample 128 and collect the resulting fluorescence emissions 124. This arrangement allows for a more compact light sheet microscopy system 100 with fewer optic components. Moreover, additional depth-of-field optics may be added or retrofitted to a conventional light sheet microscopy system 10, which would provide enhanced resolution and higher signal-to-noise ratio than images acquired by light sheet microscopy system 10.

In some embodiments, the processor 120 receives images from the fluorescence emissions 124 collected by the second objective lens 104 and the images from the fluorescence emissions 124 collected by the third objective lens 106. In the light sheet microscopy system 100, the lateral resolution of the fluorescence emissions 124 collected by the third objective lens 106 is preserved with a sacrifice in axial resolution, while images from the fluorescence emissions 124 that are collected by the second objective lens 104 have the axial resolution preserved with a sacrifice in lateral resolution. In one embodiment, the processor 120 combines the corresponding images of the fluorescent emissions 124 having the lateral resolution preserved with the images of the fluorescent emissions 124 having the axial resolution preserved to produce a combined image with enhanced axial and lateral resolution in comparison to the images from only the second objective lens 104 with the axial resolution preserved and the lateral resolution degraded.

Figure 3A:
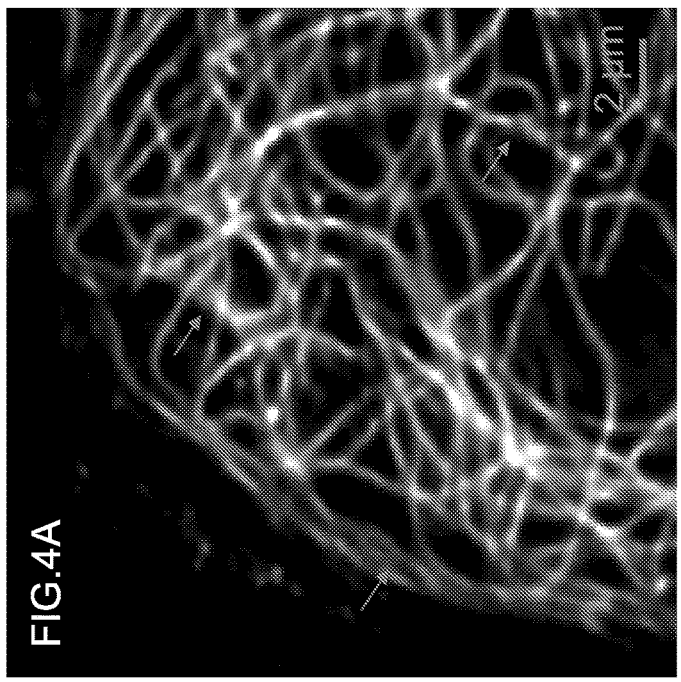
FIG. 3A is an image of microtubules taken from the embodiment of the light sheet fluorescence microscopy system of FIG. 2.
Figure 3B:
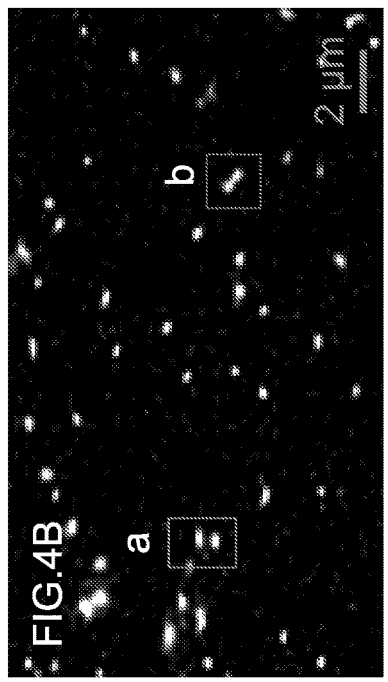
FIG. 3B is an image of beads taken from the embodiment of the light sheet fluorescence microscopy system of FIG. 2.
Figure 4A:
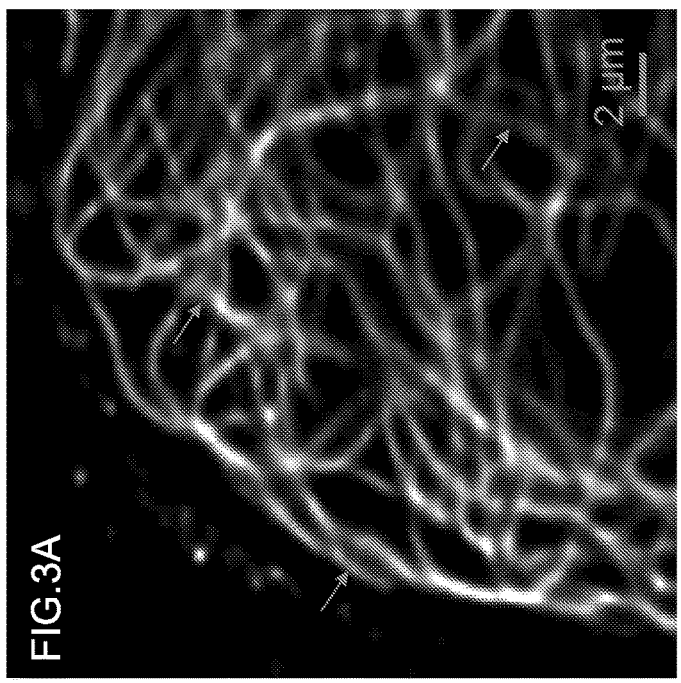
FIG. 4A is an image of microtubules taken from a conventional light sheet microscopy system.
Figure 4B:
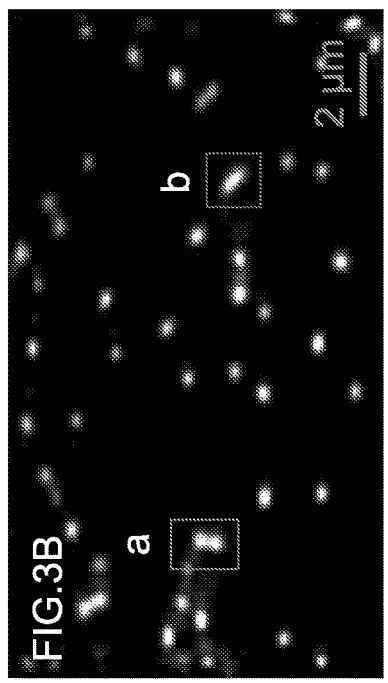
FIG. 4B is an image of beads taken from a conventional light sheet microscopy system.

Referring to FIGS. 4A and 4B, images of beads and microtubules are shown that were produced by a conventional light sheet microscopy system 10, while FIGS. 3A and 3B show images of the same beads and microtubules that were produced by the light sheet microscopy system 100. The boxes shown in FIGS. 3B and 4B and the arrows shown in FIGS. 3A and 4A highlight features that undergo resolution enhancement between the conventional light sheet microscopy system 10 and the light sheet microscopy system 100.

Figure 5:
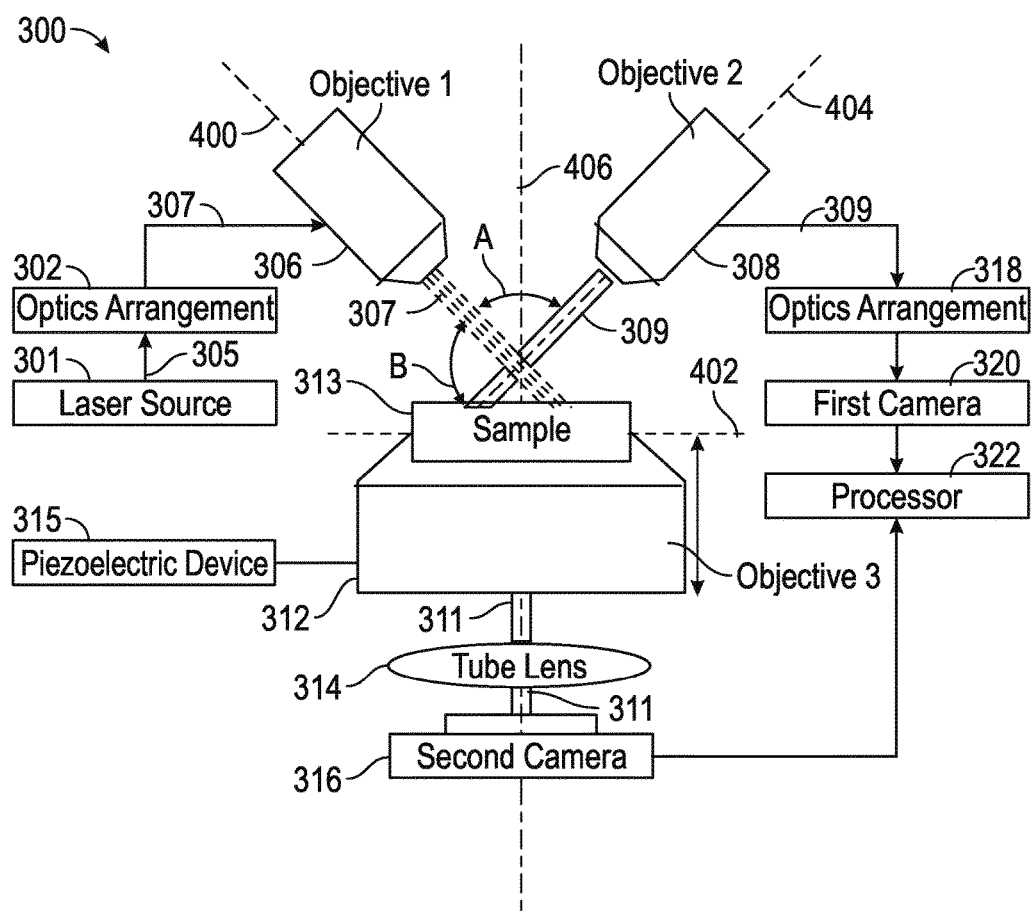
FIG. 5 is a simplified block diagram showing another embodiment of a light sheet microscopy system in which one of the objective lenses is oscillated to extend the depth of field.

Referring to FIG. 5, another embodiment of the light sheet microscopy system, designated 300, may include an illumination source 301, for example a laser, that generates a single light beam 305 transmitted through an optics arrangement 302 for producing an excitation light sheet 307 that is focused through a first objective lens 306 for illuminating a sample 313. The first objective lens 306 defines a longitudinal axis 400 that forms at an angle B relative to the plane 402 of the sample 313. When the sample 313 is illuminated by the excitation light sheet 307 focused on the sample 313 through the first objective lens 306, fluorescence emissions 309 and 311 are generated by the sample 313 which are detected by a second objective lens 308 defining a longitudinal axis 404 that forms a perpendicular angle A relative to longitudinal axis 400 defined by the first objective lens 306. The second objective lens 308 focuses the fluorescence emissions 309 through an optics arrangement 318 for detection through a first camera 320. The detected images of the fluorescence emissions 309 are then sent to a processor 322 having one or more applications for processing the detected images of the fluorescence emissions 309.

As further shown, fluorescence emissions 311 emitted in another direction by the sample 313 are detected by a third objective lens 312 aligned along a longitudinal axis 406 that is in perpendicular relation to plane 402 of the sample 313. In some embodiments, the third objective lens 312 is operatively connected to a piezoelectric device 315 that rapidly scans the third objective lens 312 during a time period when the light sheet 307 illuminating the sample 313 is stationary as is commonly used in acquiring "z stacks" or imaging volumes on a conventional microscope. As such, the scanning operation has been found to extend the depth of field of the third objective lens 312, thereby allowing detection or capture of the fluorescence emissions 311 from an entire light sheet for each light sheet position when the sample 313 is illuminated. In one embodiment, the third objective lens 312 is a high numerical aperture objective lens.

In some embodiments, a tube lens 314 may be arranged in 4f telescopic relation so as to image the fluorescence emissions 311 captured by the third objective lens 312 onto a second camera 316 for capturing raw images of the sample 313. In this arrangement, the raw images captured by the second camera 316 have degraded lateral resolution; however, the extended depth of field of the raw images and the fact that lateral resolution of these images may be recovered to substantially normal levels using conventional deconvolution techniques offsets any degradation of lateral resolution that occurs prior to deconvolution techniques being applied.

In some embodiments, the images from the first camera 320 and the second camera 316 are transmitted to the processor 322 and the images combined to produce a composite image with extended depth of field.

Figure 6B:
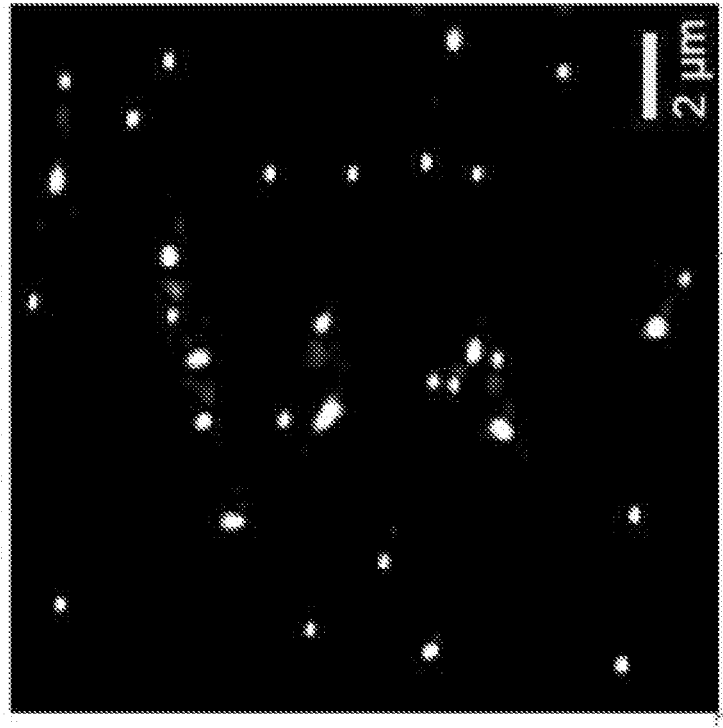
FIG. 6B is a similar image taken with a convention light sheet microscopy system.
Figure 6A:
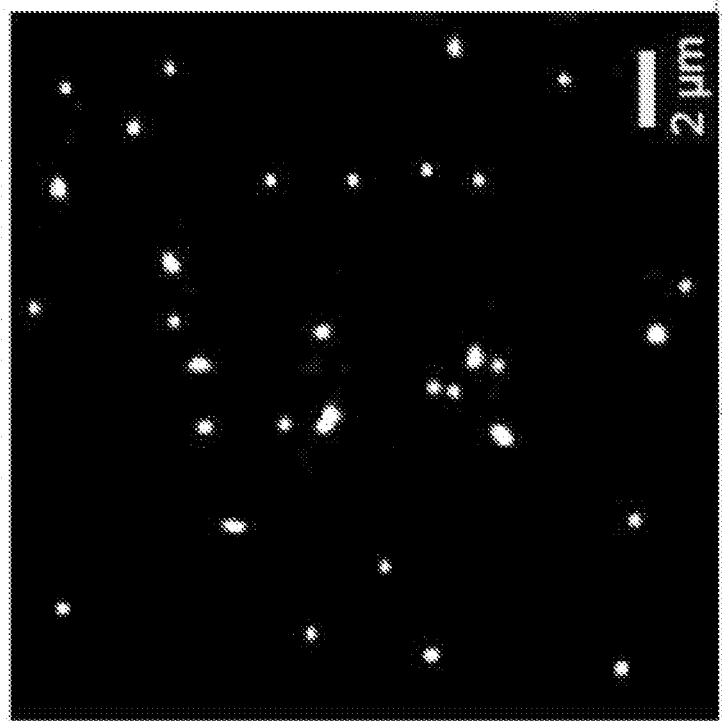
Figure 7:
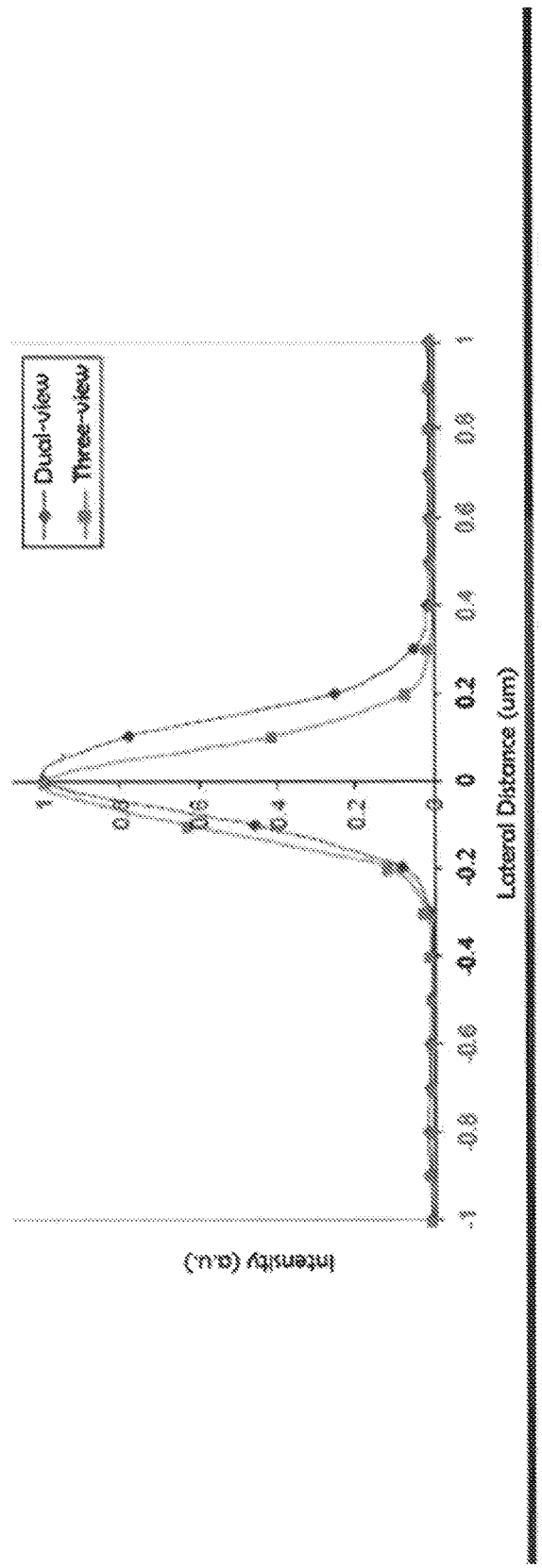
FIG. 7 is a graph showing the intensity in relation to lateral distance for illustrating the difference in resolution between the image of FIG. 6A and the image of FIG. 6B.

FIG. 6A is an image of beads taken by the light sheet microscopy system 300 with the axial movement of the third objective lens 316, while FIG. 6B is another image taken of the same beads by the conventional light sheet system 10 without the axial movement of the third objective 316. FIG. 7 is a graph that illustrates the improved resolution of a three (x-y-z axes) view arrangement as shown in FIG. 6A in comparison to the two view (x-y axes) arrangement without axial movement of the third objective 316 of FIG. 6B.

Figure 8:
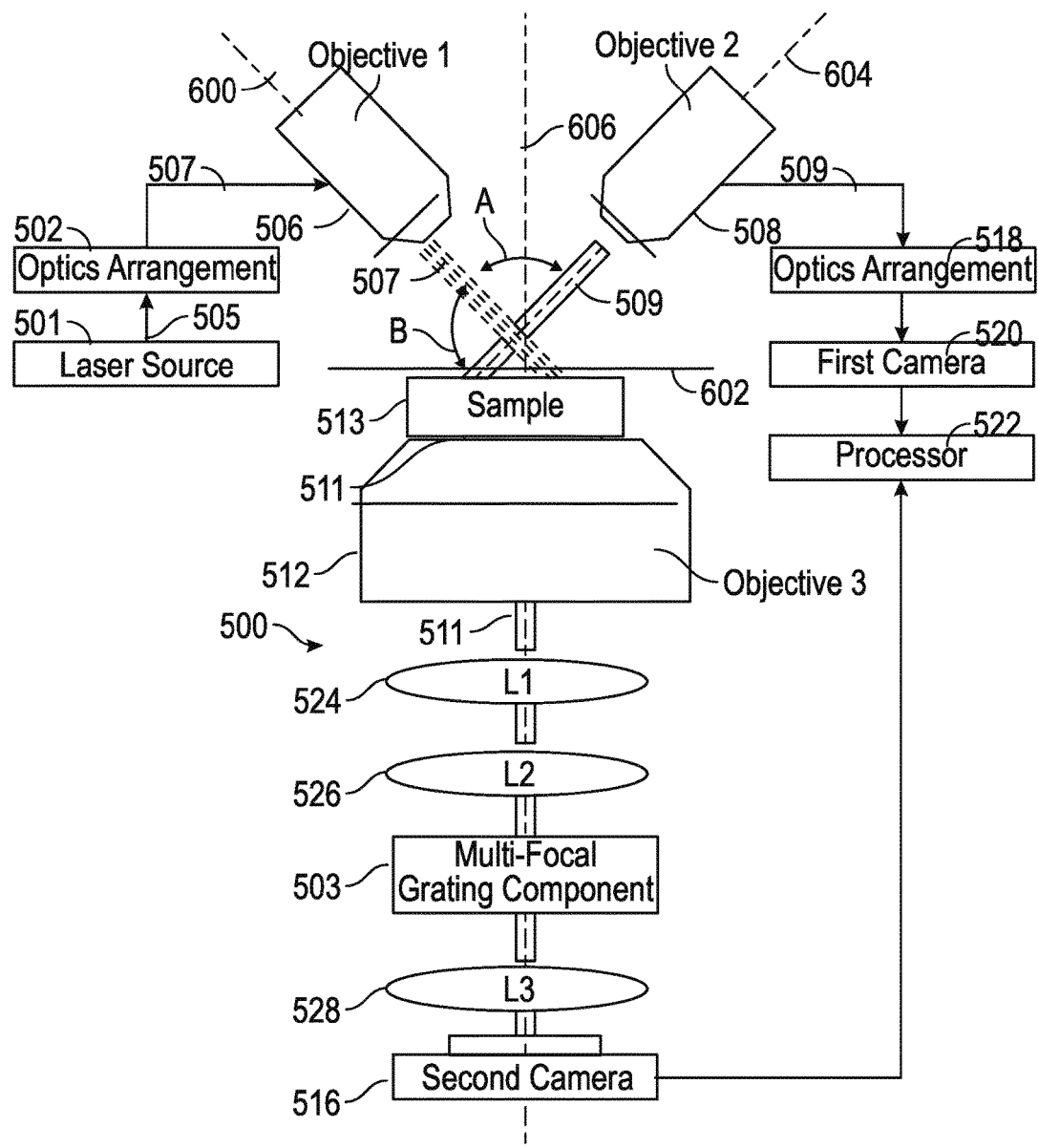
FIG. 8 is a simplified block diagram showing another embodiment of a light sheet microscopy system in which a multi-focus grating device is positioned at the fourier (back focal) plane of the third objective lens to extend the effective depth of field of the third objective lens.

Referring to FIG. 8, another embodiment of the light sheet microscopy system, designated 500, may include a multi-focus grating component 503 that is positioned at the fourier (back focal) plane of the third objective lens 512 to extend the effective depth of field of the third objective lens 512. In other embodiments, the multi-focus grating component 503 can be positioned at any plane conjugate to the back focal plane of the third objective 512.

In some embodiments, the light sheet microscopy system 500 may include an illumination source 501, for example, a laser, that generates a single light beam 505 transmitted through an optics arrangement 502 for producing an excitation light sheet 507 that is focused through a first objective lens 506 for illuminating a sample 513. The first objective lens 506 defines a longitudinal axis 600 that forms at an angle B relative to the plane 602 of the sample 513. When the sample 513 is illuminated by the excitation light sheet 507 focused on the sample 513 through the first objective lens 506, fluorescence emissions 509 and 511 are generated by the sample 513 which are detected by a second objective lens 508 defining a longitudinal axis 604 that forms a perpendicular angle A relative to longitudinal axis 600 defined by the first objective lens 506. The second objective lens 508 focuses the fluorescence emissions 509 through an optics arrangement 518 for detection through a first camera 520. The detected images of the fluorescence emissions 509 are then sent to a processor 522 having one or more applications for processing the detected images of the fluorescence emissions 509.

As further shown, fluorescence emissions 511 emitted in another direction by the sample 513 are detected by a third objective lens 512 aligned along a longitudinal axis 606 that is in perpendicular relation to plane 602 of the sample 513. A first lens 524 and a second lens 526 may be arranged in 4f configuration so as to image the back focal plane of the third objective lens 512 at the back focal plane of the second lens 526. In addition, the multi-focus grating component 503 may be positioned between the second lens 526 and a third lens 528 to separate and collapse the fluorescence emissions 511 onto a single plane. The multi-focus grating component 503 processes the fluorescence emissions 511 from the back focal plane of the second lens 526 such that the fluorescence emissions 511 from each focal plane are separated on the second camera 516, and can thus be spatially resolved as distinct depths in the sample 513. As such, the scanning operation using the multi-focus grating device 501 has been found to extend the depth of field of the third objective lens 512, thereby allowing detection or capture of the fluorescence emissions 511 from an entire light sheet for each light sheet position when the sample 513 is illuminated. In one embodiment, the third objective lens 512 is a high numerical aperture objective lens.

In some embodiments, a tube lens 514 may be arranged in 4f telescopic relation so as to image the fluorescence emissions 511 captured by the third objective lens 512 onto a second camera 516 for capturing raw images of the sample 513. In this arrangement, the raw images captured by the second camera 516 have degraded lateral resolution; however, the extended depth of field of the raw images and the fact that lateral resolution of these images may be recovered to substantially normal levels using conventional deconvolution techniques offsets any degradation of lateral resolution that occurs prior to deconvolution techniques being applied.

In some embodiments, the images from the first camera 520 and the second camera 516 are transmitted to the processor 522 and the images combined to produce a composite image with extended depth of field.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A light sheet microscopy system comprising:
a light source for transmitting a single light beam;
a first optics arrangement for relaying the single light beam and transforming the single light beam into a light sheet;
a first objective lens for focusing the light sheet into a sample for generating a first portion of fluorescence emissions and a second portion of the fluorescence emissions, the sample defining a plane;
a second objective lens in perpendicular orientation relative to the first objective lens, the second objective lens collecting a first portion of the fluorescence emissions;
a first detection component for receiving the first portion of the fluorescence emissions received from the second objective lens;

a third objective lens in perpendicular relation to the plane of the sample, the third objective lens being aligned to receive the second portion of the fluorescence emissions;

an optical system in operative communication with the third objective lens for extending the axial resolution and preserving the lateral resolution of the second portion of the fluorescence emissions;

a second detection component for receiving the second portion of the fluorescence emissions simultaneously as the first portion of the fluorescence emissions is received by the first detector; and a processor in operative communication with the first detection component and the second detection component for combining the first portion of the fluorescence emissions with the second portion of the fluorescence emissions to generate a composite image having an extended axial and lateral resolution.

2. The microscopy system of claim 1, wherein the optical system further comprises a diffractive optic that introduces aberrations to the second portion of the fluorescence emissions.

3. The microscopy system of claim 1, wherein the optical system further comprises a refractive optic having a plurality of incoherent apertures.

4. The microscopy system of claim 1, wherein the optical system comprises an extended depth-of-focus optic arrangement that extends either the axial resolution or the lateral resolution of the second portion of the fluorescence emissions.

5. The microscopy system of claim 4, wherein the third objective lens is oscillated to extend either the axial resolution or the lateral resolution of the second portion of the fluorescence emissions.

6. The microscopy system of claim 1, wherein the first detection component comprises a first camera and the second detection component comprises a second camera, wherein the microscopy system further comprising a second optic arrangement for focusing the second portion of fluorescence emissions onto the second detection component and wherein the second optic arrangement comprises a first lens and a second lens in 4f telescopic relation to image the back focal plane of the third objective lens at the back focal plane of the second lens.

7. The microscopy system of claim 1, wherein the optical system comprises a cubic phase plate component.

8. The microscopy system of claim 1, wherein the optical system comprises an incoherent layer cake component.

9. The microscopy system of claim 1, wherein the optical system comprises a multi-focus grating component.

10. A method comprising:
transmitting a single light beam from an illumination source;
transforming the single light beam into a light sheet;
focusing the light sheet into a sample for generating fluorescence emissions, the sample defining a plane;
positioning a first objective lens in perpendicular relation to a second objective lens, wherein the first objective lens illuminates the sample with the light sheet for generating a first portion of fluorescence emissions and a second portion of fluorescence emissions and the second objective lens collects the first portion of the fluorescence emissions;
detecting the first portion of the fluorescence emissions received from the second objective lens;

positioning a third objective lens in perpendicular relation to the plane of the sample, the third objective lens being positioned to receive a second portion of the fluorescence emissions;

extending the axial resolution of the second portion of the fluorescence emissions and preserving the lateral resolution of the second portion of the fluorescence emissions;

detecting the second portion of the fluorescence emissions simultaneously as the first portion of the fluorescence emissions is detected by the first detector; and combining the first portion of the fluorescence emissions with the second portion of the fluorescence emissions to generate a composite image having an extended axial and lateral resolution.

11. The method of claim 10, wherein extending the axial resolution while preserving the lateral resolution of the second portion of the fluorescence emissions comprises positioning a diffractive optic in relation to the third objective lens.

12. The method of claim 10, wherein extending the axial resolution while preserving the lateral resolution of the second portion of the fluorescence emissions comprises positioning a refractive optic in relation to the third objective lens.

13. The method of claim 10, further comprising:
positioning a first lens in 4f telescopic relation with a second lens so as to image a back focal plane of the third objective lens at the back focal plane of the second lens.

14. The method of claim 13, further comprising:
positioning a third lens in 4f telescopic relation with the second lens.

15. A light sheet microscopy system comprising:
a light source for transmitting a single light beam;
a first optics arrangement for relaying the single light beam and transforming the single light beam into a light sheet;
a first objective lens for focusing the light sheet into a sample for generating a first portion of fluorescence emissions and a second portion of fluorescence emissions, the sample defining a plane;
a second objective lens in perpendicular orientation relative to the first objective lens, the second objective lens collecting a first portion of the fluorescence emissions;
a first detection component for receiving the first portion of the fluorescence emissions received from the second objective lens;
a third objective lens aligned to receive a second portion of the fluorescence emissions;
a depth of focus optic component in operative communication with the third objective lens for introducing aberrations in the second portion of the fluorescence emissions;
a second detection component for receiving the second portion of the fluorescence emissions simultaneously as the first portion of the fluorescence emissions is detected by the first detector; and
a processor in operative communication with the first detection component and the second detection component for combining the first portion of the fluorescence emissions with the second portion of the fluorescence emissions to generate a composite image with increased resolution.

16. The light sheet microscopy system of claim 15, wherein introducing aberrations in the second portion of the fluorescence emissions degrades the axial resolution of the second portion of the fluorescence emissions.

17. The light sheet microscopy system of claim 15, wherein introducing aberrations in the second portion of the fluorescence emissions substantially preserves the lateral resolution of the second portion of the fluorescence emissions.

18. The light sheet microscopy system of claim 15, wherein the composite image combines the axial resolution of the first portion of the fluorescent emissions with the lateral resolution of the second portion of the fluorescent emissions.

19. The light sheet microscopy system of claim 1 wherein the third objective lens being movable along the longitudinal axis for performing a scanning operation that receives a second portion of the fluorescence emissions.

20. The light sheet microscopy system of claim 19, further comprising: a piezoelectric device for causing movement of the third objective lens along the longitudinal axis.

* * * * *